(12) United States Patent
Sakai et al.

(10) Patent No.: US 6,332,966 B1
(45) Date of Patent: Dec. 25, 2001

(54) AIR/FUEL RATIO DETECTING ARRANGEMENT

(75) Inventors: Shoichi Sakai; Futoshi Ichiyanagi, both of Gunma; Toshiaki Inoue, Yokohama, all of (JP)

(73) Assignees: Unisia Jecs Corporation, Atsugi; Nissan Motor Co., Ltd., Yokohama, both of (JP)

( * ) Notice: Subject to any disclaimer, the term of this patent is extended or adjusted under 35 U.S.C. 154(b) by 0 days.

(21) Appl. No.: 09/597,158

(22) Filed: Jun. 20, 2000

(30) Foreign Application Priority Data

Jun. 28, 1999 (JP) .................................................. 11-182533

(51) Int. Cl.[7] .......................... G01N 27/409; G01N 27/41
(52) U.S. Cl. .......................... 204/425; 204/426; 204/427; 204/406
(58) Field of Search ..................... 204/406, 408, 204/424, 425, 426, 427; 73/23.32; 123/672, 676, 677, 697

(56) References Cited

U.S. PATENT DOCUMENTS

| | | | |
|---|---|---|---|
| 4,707,241 | * 11/1987 | Nakagawa et al. .................. 204/406 |
| 5,236,569 | 8/1993 | Murase et al. ........................ 204/412 |
| 5,353,774 | * 10/1994 | Furuya ................................. 123/697 |
| 5,391,284 | * 2/1995 | Hoetzel ................................ 204/425 |
| 5,671,721 | * 9/1997 | Aoki ..................................... 123/697 |
| 5,895,564 | * 4/1999 | Miyate et al. ..................... 205/784.5 |

FOREIGN PATENT DOCUMENTS 3-167467    7/1991    (JP) .

* cited by examiner

Primary Examiner—Robert J. Warden, Sr.
Assistant Examiner—Kaj K. Olsen
(74) Attorney, Agent, or Firm—Foley & Lardner

(57) ABSTRACT

An A/F ratio detecting arrangement includes a sensor casing having an oxygen sensor part arranged between first and second electrodes and an oxygen pump part arranged between third and fourth electrodes, which are heated by a heater. A signal output processing circuit serves to provide an A/F ratio signal. A signal switcher serves to provide a provisional oxygen content signal derived from the first and second electrodes when the oxygen pump part is not activated yet, and the A/F ratio signal when the oxygen pump part is activated.

16 Claims, 7 Drawing Sheets

AIR/FUEL RATIO DETECTING ARRANGEMENT

BACKGROUND OF THE INVENTION

The present invention relates to an air/fuel ratio detecting arrangement for detecting the mixing ratio of intake air to fuel or air/fuel (A/F) ratio of an automotive engine, for example.

Generally, automotive engines provide an A/F ratio sensor arranged with an exhaust pipe for sensing the content of oxygen remaining in exhaust gas as A/F ratio of intake air. In order to obtain the A/F ratio close to a theoretical A/F ratio (=14.7) during engine idle operation, for example, an electronic control unit (ECU) carries out correction control of the fuel injection amount, i.e. so-called A/F ratio control.

The A/F ratio sensor arranged with the exhaust pipe constitutes an A/F ratio detecting arrangement as disclosed, for example, in U.S. Pat. No. 5,236,569 issued Aug. 17, 1993 to Murase et al. And the A/F ratio sensor includes a casing formed out of an oxygen-ion conductive material with such as zirconia (ZrO2) and having air and gas cells.

Arranged in the sensor casing are an oxygen sensor part for providing an oxygen content signal obtained in accordance with the oxygen contents in the air and gas cells and by means of a first electrode disposed on the air-cell side and a second electrode disposed on the gas-cell side, an oxygen pump part for urging oxygen ions to flow into or out of the gas cell through the sensor casing by providing an oxygen pump signal to a third electrode disposed on the gas-cell side and a fourth electrode disposed outside, and a heater for heating the oxygen sensor part and the oxygen pump part by receiving outside electric power.

The A/F ratio sensor is connected to a signal output processing circuit or A/F ratio outputting means. The signal output processing circuit provides an oxygen pump signal to the third and fourth electrodes in accordance with an oxygen content signal derived from the first and second electrodes, and it also provides to the ECU, etc. an A/F ratio signal indicative of the oxygen content in the gas cell in accordance with the electric power amount supplied to the third and fourth electrodes by the oxygen pump signal.

During engine operation and when exhaust gas flows into the gas cell of the sensor casing, oxygen ions are urged to move through the oxygen sensor part in accordance with a difference in oxygen content between the air and gas cells, generating an electromotive force or an oxygen content signal between the first and second electrodes.

The signal output processing circuit applies a voltage signal or oxygen pump signal between the third and fourth electrodes in accordance with an oxygen content signal generated between the first and second electrodes so as to urge to move oxygen ions through the oxygen pump part in such a way as to compensate a difference in oxygen content between the air and gas cells. As a result, current is passed between the third and fourth electrodes in accordance with the amount of moved oxygen ions. Using a value of this current or pump current, a voltage value of an oxygen pump signal, etc., the signal output processing circuit provides an A/F ratio signal indicative of the A/F ratio of intake air.

Through the A/F ratio signal, the ECU can receive the A/F ratio of intake air as a continuous value, based on which accurate A/F ratio control can be ensured to obtain the A/F ratio close to the theoretical A/F ratio.

In the above A/F ratio detecting arrangements, upon engine start, etc., the oxygen sensor part and the oxygen pump part are heated by the heater for their quick activation. Upon engine start, for example, the two parts are heated up to about 550° C. during at least 18–20 sec. so as to make the A/F ratio detectable.

In the A/F ratio detecting arrangements, as described above, upon engine start, for example, the oxygen sensor part and the oxygen pump part are heated by the heater up to about 550° C. for their quick activation. This means that upon engine start, a time of at least 18–20 sec. is needed from start of heating to full activation of the two parts. Additionally, when the oxygen pump part is not activated yet, the signal output processing circuit provides an A/F ratio signal having roughly the same output value as that when the A/F ratio is close to the theoretical A/F ratio. It is thus difficult to early determine whether or not the oxygen pump part is activated by the simple use of the A/F ratio signal.

Therefore, in the above A/F ratio detecting arrangements, detection of the A/F ratio is often started after a wait of about 18–20 sec., during which the oxygen pump part seems to fully be activated. This disallows early commencement of A/F ratio control during idle operation upon engine start, etc., resulting in tendency to poor purification of exhaust gas, etc.

SUMMARY OF THE INVENTION

It is, therefore, an object of the present invention to provide an A/F ratio detecting arrangement which contributes to early commencement of detection of the A/F ratio of intake air, stable detection thereof, and improvement in detection accuracy and reliability in the initial stage.

One aspect of the present invention lies in providing an arrangement for detecting an air/fuel (A/F) ratio, comprising:

a sensor casing having an air cell and a gas cell into which exhaust gas flows;

first, second, third and fourth electrodes located in said air cell, said gas cell, said gas cell, and outside, respectively;

an oxygen sensor part arranged with said sensor casing, said oxygen sensor part providing an oxygen content signal indicative of a difference in oxygen content between said air cell and said gas cell through said first and second electrodes;

an oxygen pump part arranged with said sensor casing, said oxygen pump part urging oxygen ions to flow into and out of said gas cell through said sensor casing in accordance with an oxygen pump signal received between said third and fourth electrodes;

a heater arranged with said sensor casing, said heater heating said oxygen sensor part and said oxygen pump part;

a processing circuit which provides said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

a signal switching circuit which provides in a switched way either of said A/F ratio signal and one of said oxygen content signal and a provisional oxygen content signal derived from said first and fourth electrodes; and an electronic control unit (ECU) which provides, upon determination of activation of said oxygen pump part in accordance with either of said oxygen content signal and said provisional oxygen content signal, a switching signal to said signal switching circuit for providing said A/F ratio signal.

Another aspect of the present invention lies in providing an arrangement for detecting an air/fuel (A/F) ratio, comprising:

a sensor casing having an air cell and a gas cell into which exhaust gas flows;

first, second, third and fourth electrodes located in said air cell, said gas cell, said gas cell, and outside, respectively;

an oxygen sensor part arranged with said sensor casing, said oxygen sensor part providing an oxygen content signal indicative of a difference in oxygen content between said air cell and said gas cell through said first and second electrodes;

an oxygen pump part arranged with said sensor casing, said oxygen pump part urging oxygen ions to flow into and out of said gas cell through said sensor casing in accordance with an oxygen pump signal received between said third and fourth electrodes;

a heater arranged with said sensor casing, said heater heating said oxygen sensor part and said oxygen pump part;

a processing circuit which provides said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

a signal amplifier circuit which amplifies said A/F ratio signal to provide an amplified A/F ratio signal;

a signal switching circuit which provides in a switched way either of said A/F ratio signal and said amplified A/F ratio signal; and an electronic control unit (ECU) which provides, upon determination of activation of said oxygen pump part in accordance with said amplified A/F ratio signal, a switching signal to said signal switching circuit for providing said A/F ratio signal.

Still another aspect of the present invention lies in providing an arrangement for detecting an air/fuel (A/F) ratio, comprising:

a sensor casing having an air cell and a gas cell into which exhaust gas flows;

first, second, third and fourth electrodes located in said air cell, said gas cell, said gas cell, and outside, respectively;

an oxygen sensor part arranged with said sensor casing, said oxygen sensor part providing an oxygen content signal indicative of a difference in oxygen content between said air cell and said gas cell through said first and second electrodes;

an oxygen pump part arranged with said sensor casing, said oxygen pump part urging oxygen ions to flow into and out of said gas cell through said sensor casing in accordance with an oxygen pump signal received between said third and fourth electrodes;

a heater arranged with said sensor casing, said heater heating said oxygen sensor part and said oxygen pump part;

means for providing said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

means for providing in a switched way either of said A/F ratio signal and one of said oxygen content signal and a provisional oxygen content signal derived from said first and fourth electrodes; and means for providing, upon determination of activation of said oxygen pump part in accordance with either of said oxygen content signal and said provisional oxygen content signal, a switching signal to said signal switching circuit for providing said A/F ratio signal.

A further aspect of the present invention lies in providing an arrangement for detecting an air/fuel (A/F) ratio, comprising:

a sensor casing having an air cell and a gas cell into which exhaust gas flows;

first, second, third and fourth electrodes located in said air cell, said gas cell, said gas cell, and outside, respectively;

an oxygen sensor part arranged with said sensor casing, said oxygen sensor part providing an oxygen content signal indicative of a difference in oxygen content between said air cell and said gas cell through said first and second electrodes;

an oxygen pump part arranged with said sensor casing, said oxygen pump part urging oxygen ions to flow into and out of said gas cell through said sensor casing in accordance with an oxygen pump signal received between said third and fourth electrodes;

a heater arranged with said sensor casing, said heater heating said oxygen sensor part and said oxygen pump part;

means for providing said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

means for amplifying said A/F ratio signal to provide an amplified A/F ratio signal;

means for providing in a switched way either of said A/F ratio signal and said amplified A/F ratio signal; and means for providing, upon determination of activation of said oxygen pump part in accordance with said amplified A/F ratio signal, a switching signal to said signal switching circuit for providing said A/F ratio signal.

DETAILED DESCRIPTION OF THE INVENTION

Referring to FIGS. 1–8, a description will be made with regard to an A/F ratio detecting arrangement embodying the present invention.

Figure 1:
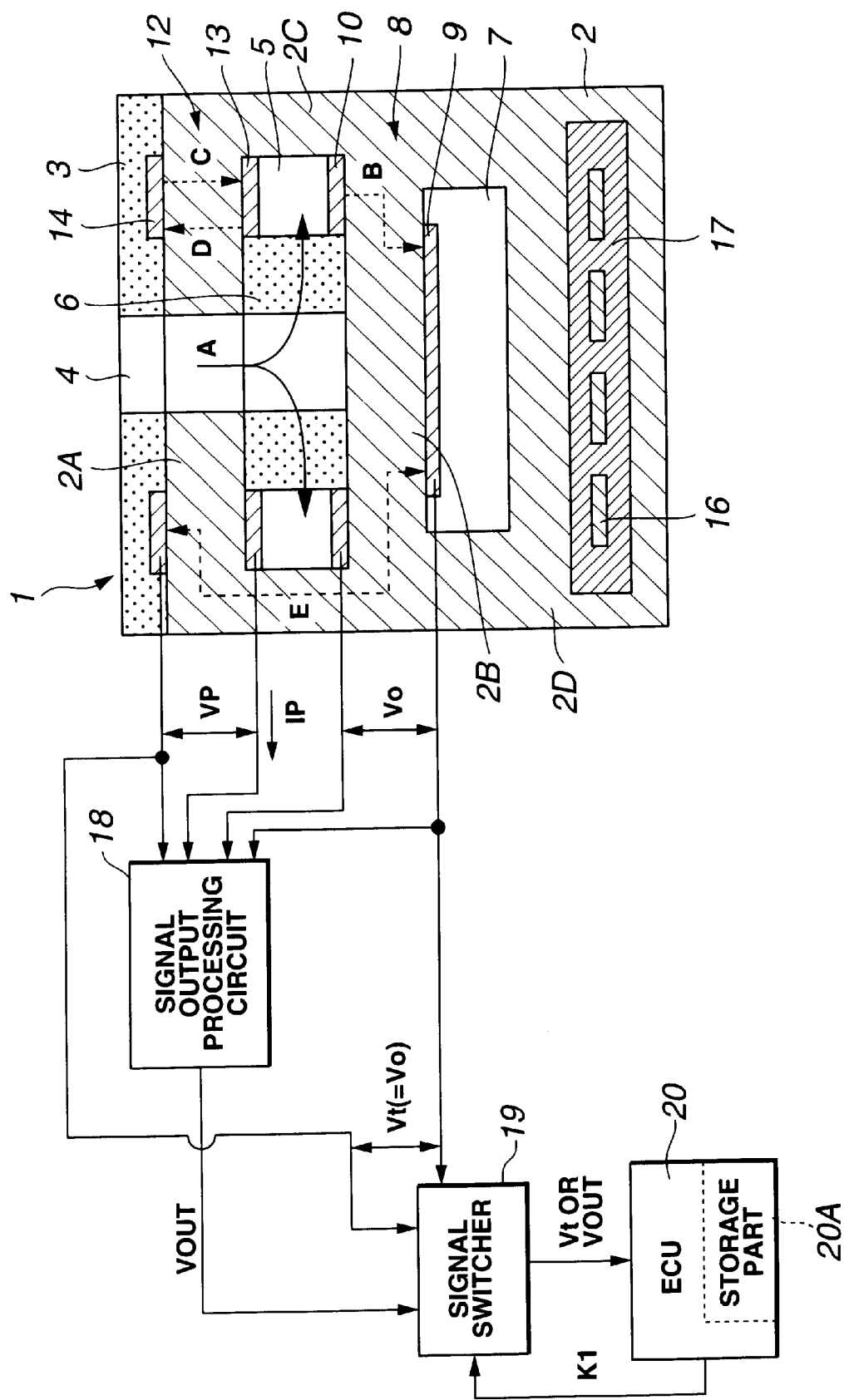
FIG. 1 is a block diagram, with cross section, showing a first embodiment of an A/F ratio detecting arrangement according to the present invention.

FIGS. 1–5 show a first embodiment of the present invention. Referring to FIG. 1, an A/F sensor 1 is arranged, for example, with an engine exhaust pipe, not shown, and includes a sensor casing 2, a Vo cell or oxygen sensor part 8, an Ip cell or oxygen pump part 12, and a heater 1 as will be described later.

The sensor casing 2 is integrally formed out of an oxygen-ion conductive material with such as zirconia ($ZrO_2$), and includes a $ZrO_2$ upper part 2A, a Vo cell or middle part 2B, a $ZrO_2$ middle part 2C, and a lower part 2D. A breathable protective layer 3 is arranged on the upper surface of the upper part 2A through an electrode 14 as will be described later.

Formed in the center of the upper part 2A is an exhaust gas guide hole 4 for introducing exhaust gas into the sensor casing 2. A diffusion gas cell 5 is defined between the upper part 2A and the Vo cell 2B to surround the guide hole 4. The diffusion gas cell 5 communicates with the guide hole 4 through a diffusion layer 6 of porous zirconia, for example. In this case, the diffusion layer 6 serves to stabilize outputs of an oxygen pump signal Vp, etc. Specifically, when oxygen ions flow into or out of the diffusion gas cell 5 through the upper part 2A by operation of the Ip cell 12 as will be described later, the diffusion layer 6 compares the inflow or outflow velocity of those oxygen ions and the inflow velocity of exhaust gas which flows into the diffusion gas cell 5 through the guide hole 4 so as to provide a certain lag to the latter.

Outside the diffusion gas cell 5, the upper part 2A and the Vo cell 2B are integrally connected by the middle part 2C. An air cell 7, which is cut off from the diffusion gas cell 5, is defined between the Vo cell 2B and the lower part 2D. Clean air is introduced into the air cell 7 from the outside of the exhaust pipe.

The Vo cell 8 is arranged with the sensor casing 2, and includes the Vo cell 2B of the sensor casing 2, a first electrode 9 located in the air cell 7 and attached to the lower surface of the Vo cell 2B and a second electrode 10 located in the diffusion gas cell 5 and attached to the upper surface of the Vo cell 2B.

During engine operation, exhaust gas flows into the diffusion gas cell 5 through the guide hole 4 and the diffusion layer 6 as illustrated by arrow A in FIG. 1, oxygen ions are urged to move in accordance with a difference in oxygen content between the diffusion gas cell 5 and the air cell 7 through the Vo cell 2B of the sensor casing 2 as illustrated by arrow B in FIG. 1, thereby generating an electromotive force between the electrodes 9, 10. The Vo cell 8 provides this electromotive force or an oxygen content signal Vo to an after-mentioned signal output processing circuit 18.

Figure 2:
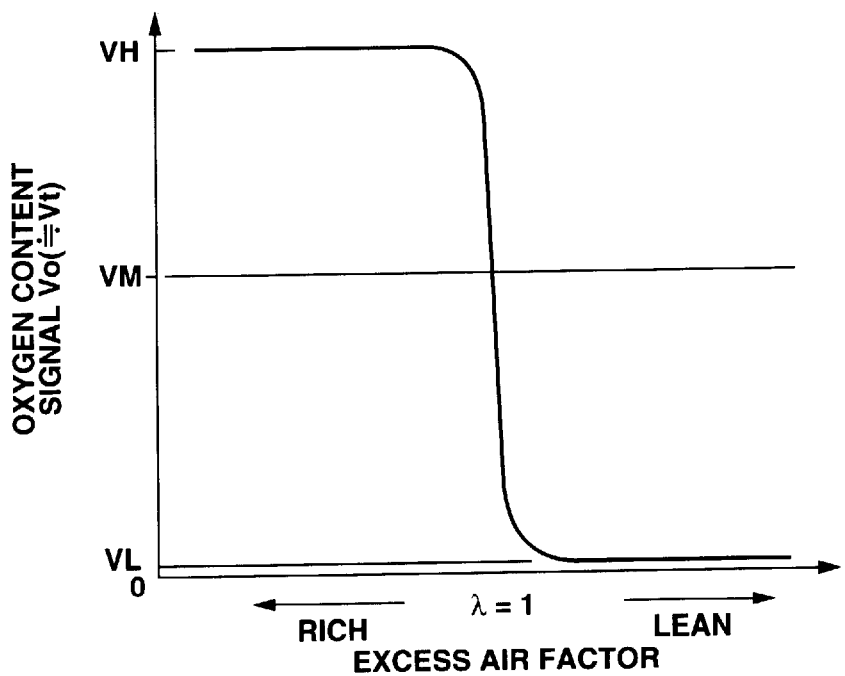
FIG. 2 is a graphical representation illustrating the relation between an oxygen content signal derived from an oxygen sensor part and the excess air factor.

Referring to FIG. 2, if the A/F ratio of engine intake air is smaller than the theoretical A/F ratio (=14.7) to show so-called rich tendency (excess air factor $\lambda<1$), the content of oxygen remaining in exhaust gas is smaller, so that the oxygen content signal Vo indicates a high level voltage $V_H$ which corresponds to a voltage value of about 1 V. On the other hand, if the A/F ratio is smaller than the theoretical A/F ratio to show so-called lean tendency, the oxygen content signal Vo indicates a low level voltage $V_L$ which is close to 0 V. When the A/F ratio is close to the theoretical A/F ratio ($\lambda \approx 1$), the oxygen content signal Vo is maintained at a medium level voltage $V_M$ which corresponds to about 400–500 mV for example.

Figure 4:
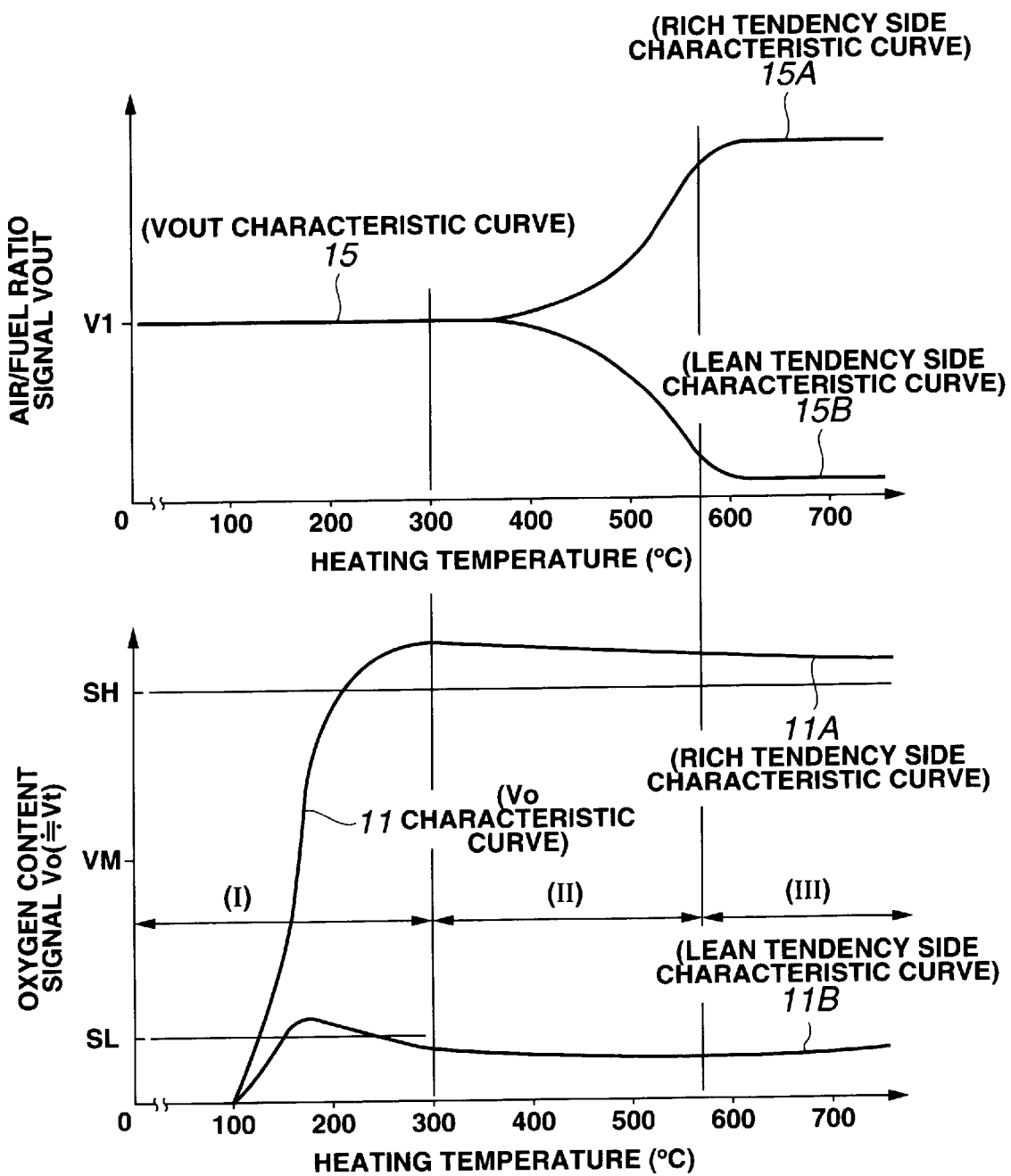
FIG. 4 is a view similar to FIG. 3, illustrating the relation between the oxygen content signal and A/F ratio signal and a heating temperature after engine start.

Referring to FIG. 4, by heating the Vo cell 8 from a room temperature to a temperature of, e.g. about 300–360° C. by the heater 16, the oxygen content signal Vo (see Vo characteristic curve 11 in FIG. 4) is bifurcate into a rich tendency side characteristic curve 11A and a lean tendency side characteristic curve 11B in accordance with the content of oxygen in exhaust gas, obtaining activation of the Vo cell 8. Therefore, in after-mentioned activation determination processing for the Vo cell 8, it is determined whether or not the Vo cell 8 is activated based on comparison of the oxygen content signal Vo with the predetermined evaluation values $S_H$, $S_L$.

The Ip cell 12 is arranged with the sensor casing 2, and includes the upper part 2A of the sensor casing 2, a third electrode 13 located in the diffusion gas cell 5 and attached to the lower surface of the upper part 2A, and a fourth electrode 14 located outside and attached to the upper surface of the upper part 2A.

When the signal output processing circuit 18 provides an oxygen pump signal Vp or a voltage signal to the electrodes 13, 14 as will be described later, the Ip cell 12 urges oxygen ions to flow into the diffusion gas cell 5 from the outside of the sensor casing 2 through the upper part 2A as illustrated by arrow C in FIG. 1, for example. On the other hand, when application of voltage based on the oxygen pump signal Vp is carried out in the opposite direction, oxygen ions flow from the diffusion gas cell 5 to the outside of the sensor casing 2 through the upper part 2A as illustrated by arrow D in FIG. 1. In this case, the amount of oxygen ions moving through the upper part 2A is determined in accordance with a difference in oxygen content between the diffusion gas cell 5 and the air cell 7. A pump current Ip id proportional to the above amount is provided to the electrodes 13, 14.

Figure 3:
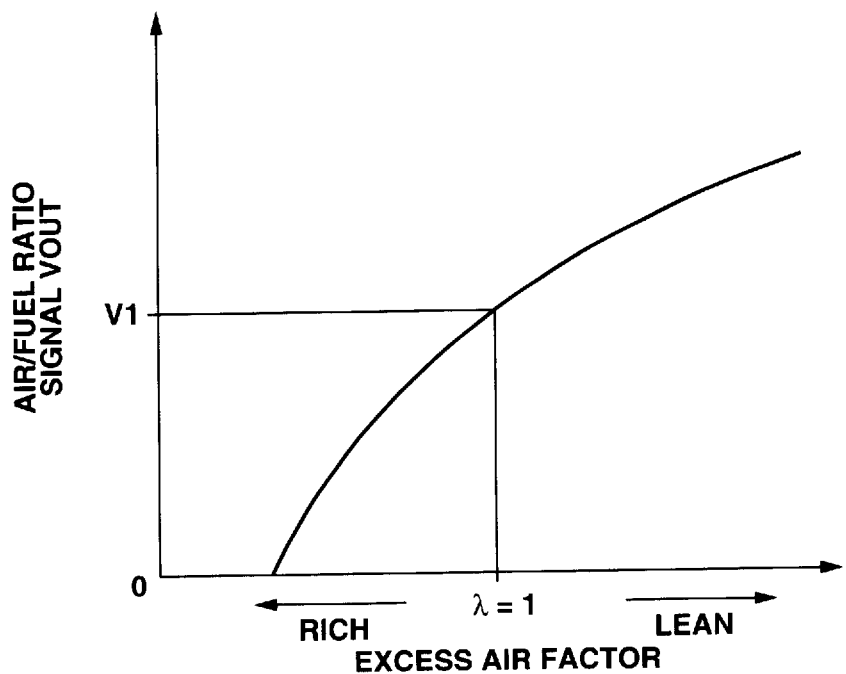
FIG. 3 is a view similar to FIG. 2, illustrating the relation between an A/F ratio signal derived from an oxygen pump part and an excess air factor.

Referring to FIG. 3, an A/F ratio signal $V_{OUT}$ using the oxygen pump signal Vp and the pump current Ip and derived from the signal output processing circuit 18 varies continuously with the A/F ratio of intake air or the oxygen content in the diffusion gas cell 5. When the A/F ratio is close to the theoretical A/F ratio, the A/F ratio signal $V_{OUT}$ corresponds to a predetermined medium level voltage V1. In this case, the medium level voltage V1 is set as a certain voltage value of 1.5–2.5 V, for example.

Referring to FIG. 4, the Ip cell 12 is activated by heating it to a temperature of, e.g. about 550° C. by the heater 16 as illustrated by a characteristic curve 15. Specifically, when the Ip cell 12 is not activated yet, the A/F ratio signal $V_{OUT}$ is provided as a certain voltage, e.g. 1.5 or 2.5 V, substantially equal to the medium level voltage V1 regardless of the oxygen content in the diffusion gas cell 5. On the other hand, when the Ip cell 12 is activated, the A/F ratio signal $V_{OUT}$ is bifurcated into a rich tendency side characteristic curve 15A and a lean tendency side characteristic curve 15B in accordance with the content of oxygen in the exhaust gas.

The electrode 14 of the Ip cell 12 and the electrode 9 of the Vo cell 8 are opposite to each other through the upper part 2A, the Vo cell 2B, and the middle part 2C of the sensor casing 2. As a result, oxygen ions are urged to move between the electrodes 9, 14 in accordance with a difference in oxygen content between exhaust gas outside the sensor casing 2 and air in the air cell 7 as shown by arrow E in FIG. 1. This produces a provisional oxygen content signal Vt which varies in substantially the same way as the oxygen content signal Vo, and is provided to an after-mentioned signal switcher 19.

The heater 16 is arranged in the lower part 2D through an insulation layer 17, and is made of a metallic material such as platinum. The heater 16 serves to electrically heat the Vo cell 8 and the Ip cell 12 by operation of an after-mentioned electronic control unit (ECU) 20.

The signal output processing circuit 18 or A/F ratio outputting means is connected to the electrodes 9, 10, 13, 14, and provides the oxygen pump signal Vp indicative of a direction of application and value of voltage in accordance with the oxygen content signal Vo derived from the Vo cell 8. A direction of application and value of voltage of the oxygen pump signal Vp are controlled by the signal output processing circuit 18 so that the oxygen content signal Vo approaches the medium level voltage $V_M$, i.e. oxygen ions are urged to move in either of the directions as illustrated by arrows C, D in FIG. 1, which can compensate a difference in oxygen content between the diffusion gas cell 5 and the air cell 7.

Using the oxygen pump signal Vp and the pump current Ip due to movement of oxygen ions, the signal output processing circuit 18 determines the oxygen content in the diffusion gas cell 5, which is provided as the A/F ratio signal $V_{OUT}$ varying continuously with the A/F ratio of intake air as shown in FIG. 3.

The signal switcher 19 or signal switching means has the input side to which the signal output processing circuit 18 and the electrodes 9, 14 are connected in parallel. The signal switcher 19 is switched by a switching signal K1 derived from the ECU 20 so as to provide to the ECU 20 in a switched way either of the A/F ratio signal $V_{OUT}$ derived from the signal output processing circuit 18 and the provisional oxygen content signal Vt derived from the electrodes 9, 14.

The ECU 20 or switch controlling means is connected to the signal switcher 19, and includes a storage part 20A consisting of ROM, RAM, etc. and having previously stored information such as after-mentioned programs for activation determination processing and A/F ratio control and data values such as evaluation values $S_H$, $S_L$, medium level voltages $V_M$, $V_1$, and time To.

Upon engine start, for example, using the provisional oxygen content signal Vt derived from the signal switcher 19, the ECU 20 carries out activation determination processing for the Vo cell 8 as will be described later. Until the predetermined time To of, e.g. about 4–5 sec. elapses after the Vo cell 8 is activated by the heater 16, the ECU 20 carries out A/F ratio control of intake air using the provisional oxygen content signal Vt.

When the predetermined time To of, e.g. 4–5 sec. elapsed after activation of the Vo cell 8, the ECU 20 determines that the Ip cell 12 is also activated, and provides the switching signal K1 to the signal switcher 19, which allows the ECU 20 to carry out A/F ratio control using the A/F ratio signal $V_{OUT}$.

Figure 5:
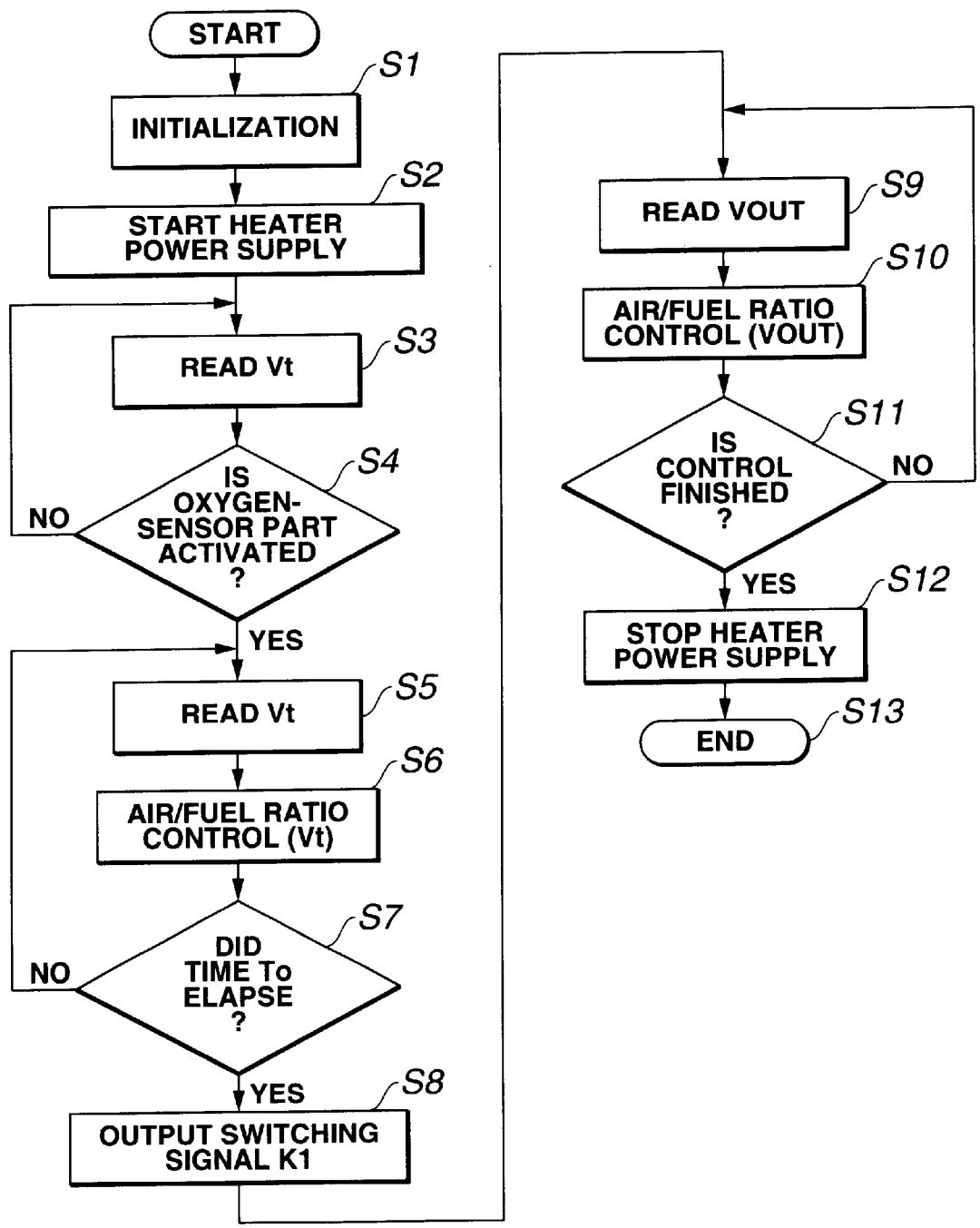
FIG. 5 is a flowchart showing operation of the first embodiment.

Referring to FIG. 5, operation of the first embodiment of the A/F ratio detecting arrangement will be described.

At a step S1, when the ECU 20 is turned on, the signal switcher 19 is initialized so that the provisional oxygen content signal Vt derived from the electrodes 9, 14 is provided to the ECU 20. At a step S2, power supply is started to the heater 16.

At a step S3, the provisional oxygen content signal Vt is read from the signal switcher 19. At a step S4, it is determined whether or not the Vo cell 8 is activated by heating of the heater 16. In this activation determination processing, when the provisional oxygen content signal Vt having a temperature characteristic roughly identical to that of the oxygen content signal Vo as shown in FIG. 4 exceeds the rich side evaluation value $S_H$, or it falls below the lean side evaluation value $S_L$ after exceeding it once, it is determined that the Vo cell 8 is activated by a temperature rise. Otherwise, it is determined that the Vo cell 8 is not activated yet.

If answer at the step S4 is NO, flow returns to the step S3 to wait for activation of the Vo cell 8. In this case, since both the Vo cell 8 and the Ip cell 12 are not activated yet, the provisional oxygen content signal Vt and the A/F ratio signal $V_{OUT}$ are in the output state given by a temperature area (I) in FIG. 4. It is thus understood that A/F ratio control is not possible in the temperature area (I).

On the other hand, if answer at the step S4 is YES, i.e. it is determined that the Vo cell 8 is activated, flow proceeds to a step S5 where the provisional oxygen content signal Vt is read. In this case, the provisional oxygen content signal Vt and the A/F ratio signal $V_{OUT}$ are in the output state given by a temperature area (II) in FIG. 4.

At a step S6, A/F ratio control is carried out using the provisional oxygen content signal Vt. Specifically, in A/F ratio control, the provisional oxygen content signal Vt is compared with the medium level voltage $V_M$, for example. If the A/F ratio of intake air shows a rich tendency, the fuel injection amount is corrected to decrease, whereas if the A/F ratio shows a lean tendency, the fuel injection amount is corrected to increase. Thus, the A/F ratio during idle operation, for example, is maintained at a value close to the theoretical A/F ratio.

At a step S7, it is determined whether or not the predetermined time To of, e.g. about 4–5 sec. elapsed after activation of the Vo cell 8. If answer at the step S7 is NO, i.e. it is determined that the Ip cell 12 is not activated yet, A/F ratio control is continuously carried out at the steps S5, S6 using the provisional oxygen content signal Vt.

On the other hand, if answer at the step S7 is YES, i.e. it is determined that the Ip cell 12 is also activated by heating of the heater 16, flow proceeds to a step S8 where the switching signal K1 is provided to the signal switcher 19. At this time, the Vo cell 8 and the Ip cell 12 are both activated, so that the provisional oxygen content signal Vt and the A/F ratio signal $V_{OUT}$ are in the output state given by a temperature area (III) in FIG. 4.

This allows the ECU 20 to receive the A/F ratio signal $V_{OUT}$ from the signal output processing circuit 18 through the signal switcher 19. Thus, at a step S9, the A/F ratio signal $V_{OUT}$ is read, and at a subsequent step S10, A/F ratio control is carried out using the A/F ratio signal $V_{OUT}$. At a step S11, A/F ratio control is repeatedly carried out until control flow of the ECU 20 is finished by turn-off, for example. When control flow is finished, flow proceeds to a step S12 where power supply is stopped to the heater 16, then flow proceeds to a step S13 to come to an end.

In the first embodiment, the A/F ratio detecting arrangement comprises the A/F ratio sensor 1, signal output processing circuit 18, signal switcher 19, and ECU 20, so that upon engine start, for example, with the Vo cell 8 and the Ip cell 12 being heated by the heater 16, it can be determined by the ECU 20 whether or not the Vo cell 8 is activated using the provisional oxygen content signal Vt which is roughly identical to the oxygen content signal Vo.

If it is determined that the Vo cell 8 is activated, A/F ratio control using the provisional oxygen content signal Vt can be started in the temperature area (II) in FIG. 4, for example. Moreover, when the predetermined time To of, e.g. 4–5 sec. elapsed after start of A/F ratio control using the provisional oxygen content signal Vt, it can be determined that the Ip cell 12 comes into the temperature area (III) in FIG. 4, and is activated already. This allows A/F ratio control using the A/F ratio signal VOUT to be started.

In the earlier art, A/F ratio control could not be carried out during a period of time from start of heating by the heater 16 to entry into the temperature area (III) in FIG. 4, e.g. about 18–20 sec. On the other hand, in the first embodiment, it was confirmed that only a short waiting time of, e.g. 6–7 sec. is needed from start of heating to entry into the temperature area (II) in FIG. 4, which allows early commencement of A/F ratio control upon engine start, etc.

Moreover, when the Ip cell 12 is not activated yet, activation determination of the Vo cell 8 and A/F ratio control are carried out using the provisional oxygen content signal Vt derived from the electrodes 9, 14. Thus, a difference in oxygen content between exhaust gas outside the sensor casing 2 and air in the air cell 7 can be detected directly as the provisional oxygen content signal Vt without relying upon exhaust gas flowing into the diffusion gas cell 5 through the diffusion layer 6, resulting in improved responsibility of this detection.

Specifically, when the Vo cell 8 is not activated yet, the responsibility of the oxygen content signal Vo is apt to lower with respect to a change in oxygen content in the diffusion gas cell 5 due to a time lag produced when exhaust gas passes through the diffusion layer 6. In the first embodiment, when the Vo cell 8 is not activated yet, activation determination of the Vo cell 8 can be carried out using the provisional oxygen content signal Vt. This allows accurate A/F ratio control in the temperature area (II) in FIG. 4.

Therefore, in the first embodiment, detection of the A/F ratio can early be started upon engine start, etc., which contributes not only to stable A/F ratio control, but an improvement in exhaust-gas purification performance and device reliability.

Figure 6:
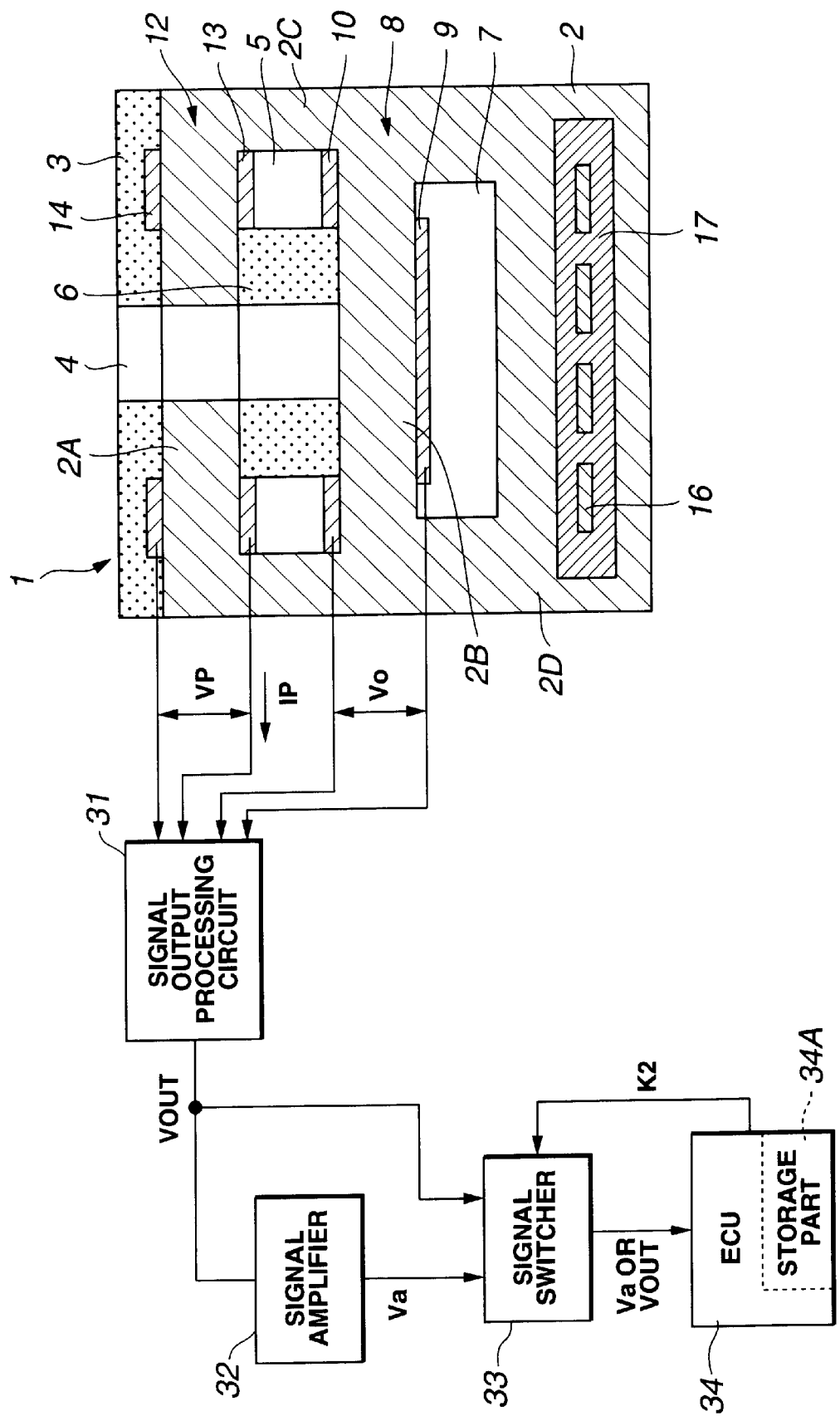
FIG. 6 is a view similar to FIG. 1, showing a second embodiment of the present invention.
Figure 7:
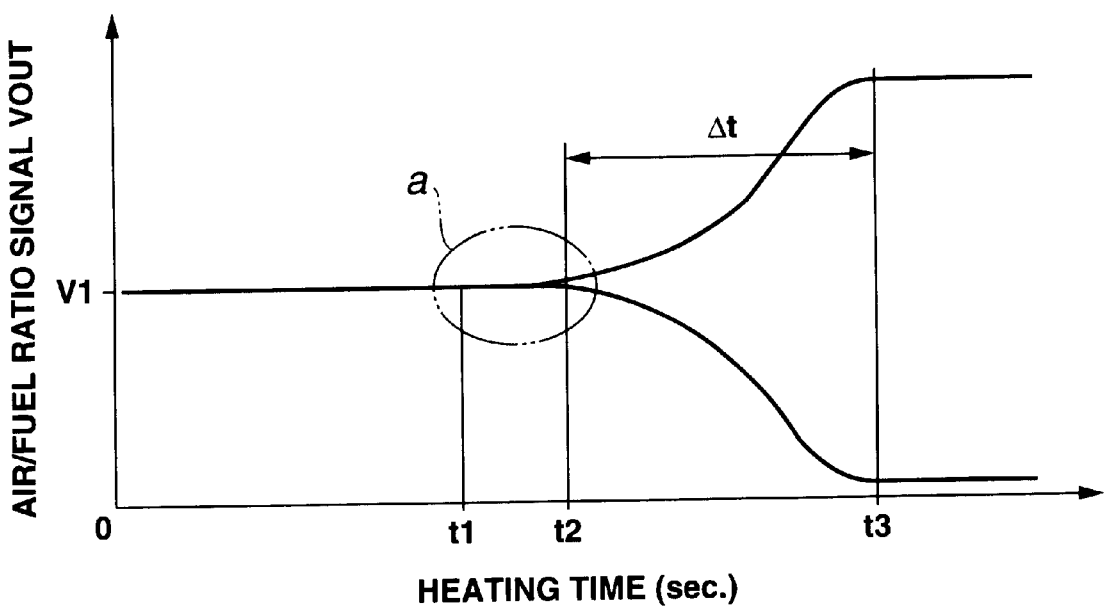
FIG. 7 is a view similar to FIG. 4, illustrating the relation between the A/F ratio signal and a heating time.
Figure 8:
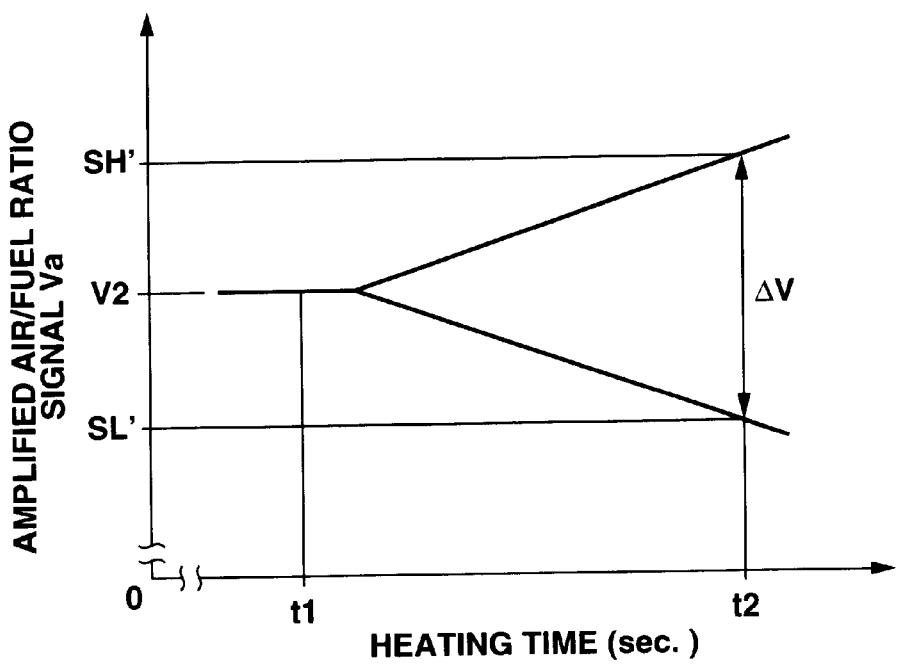
FIG. 8 is a view similar to FIG. 7, illustrating the relation between an amplified A/F ratio signal and a heating time, the amplified A/F ratio signal being obtained by amplifying the A/F ratio signal in a portion a in FIG. 7.

FIGS. 6–8 show a second embodiment of the present invention. In the second embodiment, the same reference numbers are used for features which are common to the first embodiment as shown in FIGS. 1–5, and a redundant description is eliminated. The features of the second embodiment are that the A/F ratio signal derived from the oxygen pump part is amplified, with which activation determination of the oxygen pump part is carried out.

A signal output processing circuit 31 or A/F ratio outputting means is connected to the A/F ratio sensor 1, and serves to provide the A/F ratio signal VOUT in accordance with the oxygen content in the diffusion gas cell 5 detected by the A/F ratio sensor 1 in substantially the same way as the signal output processing circuit 18 in the first embodiment.

Referring to FIG. 7, the Ip cell 12 is not activated yet during a period of time from start of heating by the heater 16 to a time t1 in FIG. 7, e.g. about 4 sec. Thus, in the non-activated state of the Ip cell 12, the A/F ratio signal VOUT derived from the signal output processing circuit 31 is maintained at a voltage value which is roughly equal to the medium level voltage V1, e.g. about 1.5 or 2.5 V.

Activation of the Ip cell 12 starts when a time t2 of, e.g. about 5 sec. elapsed after start of heating. This makes the A/F ratio signal VOUT slightly responsive to a variation in A/F ratio of exhaust gas, etc. When the medium level voltage V1 is set at about 1.5 V, the A/F ratio signal VOUT varies in a small range of 1.225–1.725 V with respect to the voltage V1.

Activation of the Ip cell 12 is completed when a time t3 of, e.g. about 10 sec. elapsed after start of heating. The A/F ratio signal VOUT is stably bifurcated into a rich tendency side output value and a lean tendency side output value in accordance with the oxygen content in the exhaust gas.

A signal amplifier 32 as signal amplifying means is connected to the signal output processing circuit 31 on the output side, and serves to amplify the A/F ratio signal VOUT to obtain an amplified A/F ratio signal Va using the following expression:

$$Va = -\alpha \times V_{OUT} + \beta \quad (1)$$

where $\alpha$ is a predetermined amplification factor, and 8 is a fixed offset voltage of, e.g. 3.45 V.

The amplification factor $\alpha$ is determined to vary in a relatively large width $\Delta V$ of variation of about 1 V when the A/F ratio signal VOUT varies in a range of 1.225–1.725 V, for example. The offset voltage $\beta$ serves to offset a signal voltage so as to have a medium value of, e.g. about 400–500 mV preferably, about 450 mV when the amplified A/F ratio signal Va varies in a range of about 1 V.

Referring to FIG. 8, with the offset voltage $\beta$ being set at 3.45 V, the amplified A/F ratio signal Va varies in roughly the same range as that of the oxygen content signal Vo of the Vo cell 8 or the provisional oxygen content signal Vt in the first embodiment in accordance with the conditions of exhaust gas. Thus, activation determination of the Ip cell 12 as will be described later can be carried out using substantially the same evaluation values SH', SL' as the evaluation values SH, SL.

Specifically, when the A/F ratio signal VOUT varies in a range of about 1.225–1.725 V, it is achieved, by substitution of the amplification factor a $\alpha=2$ and the offset voltage $\beta=3.45$ V into the expression (1), the amplified A/F ratio signal Va varying in a range of about 0–1 V (variation width $\Delta V=1$ V) with respect to a predetermined medium level voltage V2 of, e.g. about 400–500 mV preferably, about 450 mV.

A signal switcher 33 or signal switching means is connected to the signal output processing circuit 31 and the signal amplifier 32 on the output side. The signal switcher 33 is switched by a switching signal K2 derived from an after-mentioned electronic control unit (ECU) 34 so as to provide to the ECU 34 in a switched way either of the A/F ratio signal VOUT derived from the signal output processing circuit 31 and the amplified A/F ratio signal Va derived from the signal amplifier 32.

The ECU 34 or switch controlling means includes a storage part 34A having previously stored information such as after-mentioned data values such as evaluation values SH', SL' and programs for activation determination processing, etc.

Upon engine start, for example, the ECU 20 actuates the heater 16 to heat the Vo cell 8 and the Ip cell 12, and carries out activation determination processing for the Ip cell 12 using the amplified A/F ratio signal Va derived from the signal switcher 33. When activation of the Ip cell 12 starts at the time t1 in FIG. 7 and when the A/F ratio signal VOUT varies in a small range of, e.g. about 1.225–1.725 V, the amplified A/F ratio signal Va is given by a characteristic curve in FIG. 8, obtaining amplified values with a large variation width ΔV of about 1 V.

Therefore, the ECU 34 compares the amplified A/F ratio signal Va with the predetermined evaluation values SH', SL'. If a rich side output value of the amplified A/F ratio signal Va exceeds the evaluation value SH', or a lean side output value thereof falls below the evaluation value SL', it is determined that activation of the Ip cell 12 starts.

With determination of activation starting, the ECU 34 provides the switching signal K2 to the signal switcher 33, which is switched thereby to provide the A/F ratio signal VOUT to the ECU 34. Thus, using the A/F ratio signal VOUT, the ECU 34 can start A/F ratio control when coming at the t2 which is prior to the time t3 that activation of the Ip cell 12 is completed by a time difference Δt of, e.g. about 5 sec.

In the second embodiment, the medium level voltage V1 derived from the signal output processing circuit 31 is set at about 1/5 V so that the A/F ratio signal VOUT varies in a range of 1.225–1.725 V. Alternatively, the medium level voltage V1 may be set at about 2.5 V as required. In this case, the A/F ratio signal VOUT varies in a range of about 2.225–2.725 V, so that it can be achieved, using the offset voltage β=5.45 V in the expression (1), the amplified A/F ratio signal Va varying in a range of about 0–1 V with respect to the medium level voltage V2 in substantially the same way as the second embodiment.

It is thus understood that the second embodiment can produce substantially the same effect as that of the first embodiment. Particularly, in the second embodiment, using the amplified A/F ratio signal Va obtained by amplifying the A/F ratio signal Vout, it can accurately be determined upon engine start, for example, whether or not activation of the Ip cell 12 starts in accordance with the amplified A/F ratio signal Va. Based on the result of determination, A/F ratio control using the A/F ratio signal Vout can start early at the time t2 which is prior to the earlier start time by the difference Δt, e.g. about 5 sec.

After determination of activation starting, an input signal of the ECU 34 can be switched to the A/F ratio signal VOUT by the signal switcher 33. When carrying out A/F ratio control in this state, the A/F ratio signal VOUT can have a large detection or output range and a less data amount.

It is noted that in the first embodiment, the step S4 in FIG. 5 shows a concrete example of the activation determining part or means, and the steps S7, S8 show a concrete example of the switching signal outputting part or means.

In the first embodiment, either of the A/F ratio signal VOUT derived from the Ip cell 12 and the provisional oxygen content signal Vt derived from the electrodes 9, 14 is provided in a switched way through the signal switcher 19. Alternatively, the structure may be altered as shown in FIG. 9.

Figure 9:
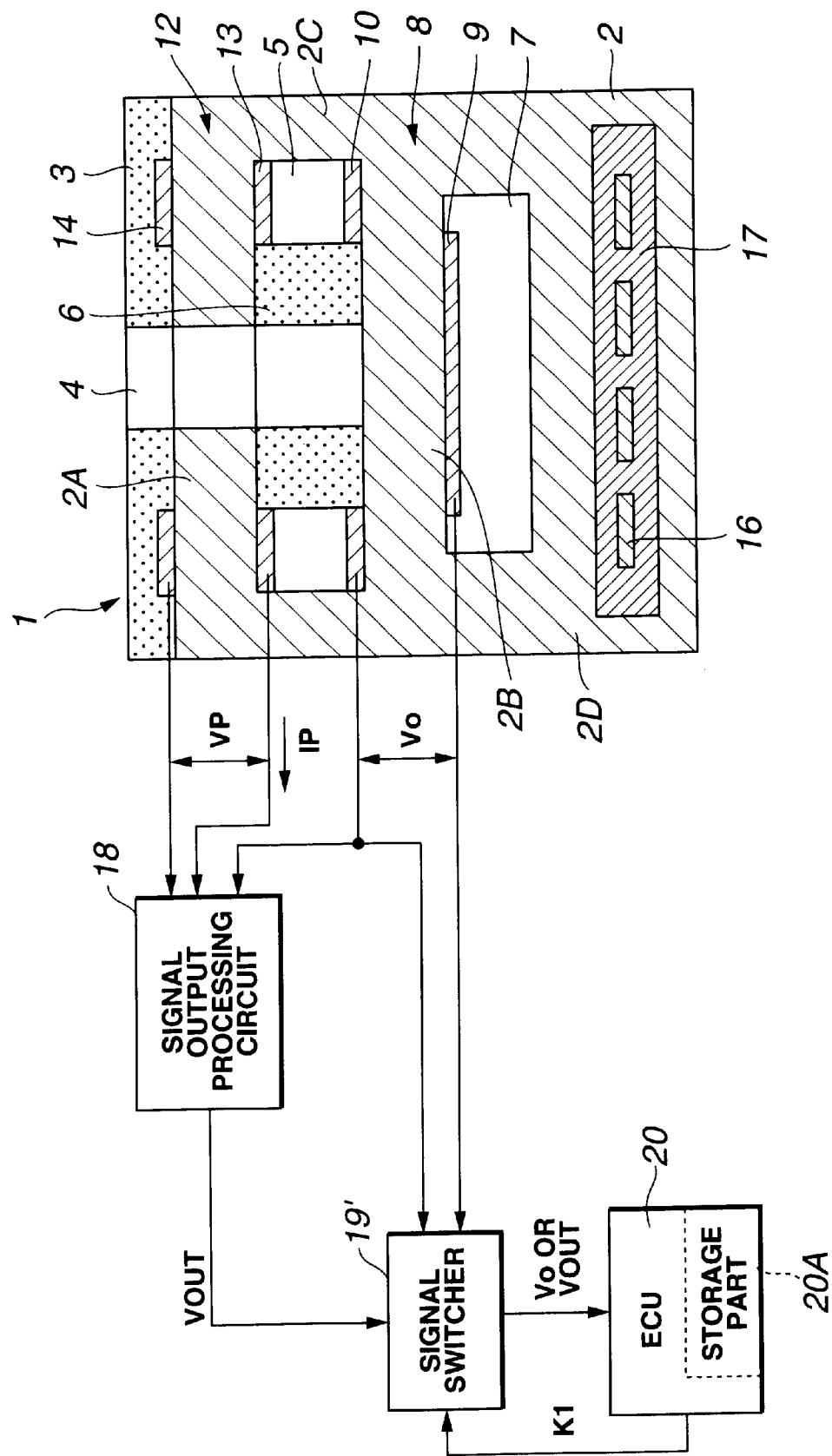
FIG. 9 is a view similar to FIG. 6, showing a variant of the first embodiment.

Specifically, referring to FIG. 9, in this variant, in place of the provisional oxygen content signal Vt derived from the electrodes 9, 14, the oxygen content signal Vo derived from the electrodes 9, 10 is provided to a signal switcher 19', and either of the oxygen content signal Vo and the A/F ratio signal VOUT is provided to the ECU 20 through the signal switcher 19'. In this variant, in control flow of the ECU 20 as shown in FIG. 5, at steps S3', S5' in place of the steps S3, S5, the oxygen content signal Vo is read, and at a step S6' in place of the step S6, A/F ratio control is carried out using the oxygen content signal Vo.

Having described the present invention with regard to the preferred embodiments, it is noted that the present invention is not limited thereto, and various changes and modifications can be made without departing from the scope of the present invention.

By way of example, in the above embodiments, the signal switcher 19, 33, the signal amplifier 32, etc. are arranged outside the ECU 20, 34. Alternatively, the A/F ratio signal VOUT derived from the signal output processing circuit 18, 31, the provisional oxygen content signal Vt derived from the electrodes 9, 14, etc. may directly be provided to the ECU 20, 34, on condition that the ECU 20, 34 carries out in a software way switching between the A/F ratio signal VOUT and the provisional oxygen content signal Vt, amplification of the A/F ratio signal VOUT, etc.

The entire contents of Japanese Pat. Application P11-182533 are hereby incorporated by reference.

What is claimed is:

1. An arrangement for detecting an air/fuel (A/F) ratio, comprising:

a casing having a gas cell into which exhaust gas flows and an air cell isolated from said gas cell, said casing including an outer periphery;

first, second, third and fourth electrodes located in said air cell, said gas cell, said gas cell and at said outer periphery, respectively;

an oxygen sensor part arranged with said casing, said oxygen sensor part providing an oxygen content signal indicative of a difference in oxygen content between said air cell and said gas cell through said first and second electrodes;

an oxygen pump part arranged with said casing, said oxygen pump part urging oxygen ions to flow into and out of said gas cell through said casing in accordance with an oxygen pump signal received between said third and fourth electrodes;

a heater arranged with said casing, said heater heating said oxygen sensor part and said oxygen pump part;

a processing circuit which provides said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

a signal switching circuit which provides either of said A/F ratio signal or one of said oxygen content signal and a provisional oxygen content signal derived from said first and fourth electrodes; and an electronic control unit (ECU) connected to said signal switching circuit, said ECU being constructed to carry out an A/F ratio control by using said provisional oxygen content signal before an activation of said oxygen sensor part is determined in accordance with either of said oxygen content signal or said provisional oxygen content signal, and to provide a switching signal to said signal switching circuit for providing said A/F ratio signal when said activation is determined.

2. The arrangement as claimed in claim 1, wherein said ECU includes an activation determining part for determining said activation of said oxygen sensor part and a switching signal outputting part for outputting said switching signal to said signal switching circuit after a lapse of a predetermined time after a determination of said activation.

3. The arrangement as claimed in claim 2, wherein said activation determining part ensures said determination of said activation when one of said oxygen content signal and said provisional oxygen content signal exceeds a predetermined rich side threshold value.

4. The arrangement as claimed in claim 2, wherein said activation determining part ensures said determination of said activation when one of said oxygen content signal and said provisional oxygen content signal falls below a predetermined lean side threshold value after exceeding said predetermined lean side threshold value once.

5. An arrangement for detecting an air/fuel (A/F) ratio, comprising:

a casing having a gas cell into which exhaust gas flows and an air cell isolated from said gas cell, said casing including an outer periphery;

first, second, third and fourth electrodes located in said air cell, said gas cell, said gas cell and at said outer periphery, respectively;

an oxygen sensor part arranged with said casing, said oxygen sensor part providing an oxygen content signal indicative of a difference in oxygen content between said air cell and said gas cell through said first and second electrodes;

an oxygen pump part arranged with said casing, said oxygen pump part urging oxygen ions to flow into and out of said gas cell through said casing in accordance with an oxygen pump signal received between said third and fourth electrodes;

a heater arranged with said casing, said heater heating said oxygen sensor part and said oxygen pump part;

a processing circuit which provides said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

a signal amplifier circuit which amplifies said A/F ratio signal to provide an amplified A/F ratio signal;

a signal switching circuit which provides either of said A/F ratio signal or said amplified A/F ratio signal; and an electronic control unit (ECU) which provides, upon determination of activation of said oxygen pump part in accordance with said amplified A/F ratio signal, a switching signal to said signal switching circuit for providing said A/F ratio signal.

6. The arrangement as claimed in claim 5, wherein said ECU ensures said determination of activation when said amplified A/F ratio signal exceeds a predetermined rich side threshold value.

7. The arrangement as claimed in claim 5, wherein said ECU ensures said determination of activation when said amplified A/F ratio signal falls below a predetermined lean side threshold value.

8. The arrangement as claimed in claim 5, wherein said signal amplifier circuit multiplies said A/F ratio signal by a predetermined amplification factor, to which a predetermined offset voltage value is added to obtain said amplified A/F ratio signal.

9. An arrangement for detecting an air/fuel (A/F) ratio, comprising:

a casing having a gas cell into which exhaust gas flows and an air cell isolated from said gas cell, said casing including an outer periphery;

first, second, third and fourth electrodes located in said air cell, said gas cell, said gas cell and at said outer periphery, respectively;

an oxygen sensor part arranged with said casing, said oxygen sensor part providing an oxygen content signal indicative of a difference in oxygen content between said air cell and said gas cell through said first and second electrodes;

an oxygen pump part arranged with said casing, said oxygen pump part urging oxygen ions to flow into and out of said gas cell through said casing in accordance with an oxygen pump signal received between said third and fourth electrodes;

a heater arranged with said casing, said heater heating said oxygen sensor part and said oxygen pump part;

means for providing said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

means for providing in a switched way either of said A/F ratio signal or one of said oxygen content signal and a provisional oxygen content signal derived from said first and fourth electrodes; and means connected to said signal switching circuit for carrying out an A/F ratio control by using said provisional oxygen content signal before an activation of said oxygen sensor part is determined in accordance with either of said oxygen content signal or said provisional oxygen content signal, and for providing a switching signal to said signal switching circuit for providing said A/F ratio signal when said activation is determined.

10. The arrangement as claimed in claim 9, wherein said means for carrying out the A/F ratio control include an activation determining part for determining said activation of said oxygen sensor part and a switching signal outputting part for outputting said switching signal to said signal switching circuit after a lapse of a predetermined time after a determination of said activation.

11. The arrangement as claimed in claim 10, wherein said activation determining part ensures said determination of said activation when one of said oxygen content signal and said provisional oxygen content signal exceeds a predetermined rich side threshold value.

12. The arrangement as claimed in claim 10, wherein said activation determining part ensures said determination of said activation when one of said oxygen content signal and said provisional oxygen content signal falls below a predetermined lean side threshold value after exceeding said predetermined lean side threshold value once.

13. An arrangement for detecting an air/fuel (A/F) ratio, comprising:

a casing having a gas cell into which exhaust gas flows and an air cell isolated from said gas cell, said casing including an outer periphery;

first, second, third and fourth electrodes located in said air cell, said gas cell, said gas cell and at said outer periphery, respectively;

an oxygen sensor part arranged with said casing, said oxygen sensor part providing an oxygen content signal indicative of a difference in oxygen content between said air cell and said gas cell through said first and second electrodes;

an oxygen pump part arranged with said casing, said oxygen pump part urging oxygen ions to flow into and out of said gas cell through said casing in accordance with an oxygen pump signal received between said third and fourth electrodes;

a heater arranged with said casing, said heater heating said oxygen sensor part and said oxygen pump part;

means for providing said oxygen pump signal to said third and fourth electrodes in accordance with said oxygen content signal and an A/F ratio signal indicative of an oxygen content in said gas cell in accordance with an electric power amount supplied to said third and fourth electrodes by said oxygen pump signal;

means for amplifying said A/F ratio signal to provide an amplified A/F ratio signal;

means for providing in a switched way either of said A/F ratio signal or said amplified A/F ratio signal; and means for providing, upon determination of activation of said oxygen pump part in accordance with said amplified A/F ratio signal, a switching signal to said signal switching circuit for providing said A/F ratio signal.

14. The arrangement as claimed in claim 13, wherein said switching signal providing means ensure said determination of activation when said amplified A/F ratio signal exceeds a predetermined rich side threshold value.

15. The arrangement as claimed in claim 13, wherein said switching signal providing means ensure said determination of activation when said amplified A/F ratio signal falls below a predetermined lean side threshold value.

16. The arrangement as claimed in claim 13, wherein said A/F ratio signal amplifying means multiply said A/F ratio signal by a predetermined amplification factor, to which a predetermined offset voltage value is added to obtain said amplified A/F ratio signal.

* * * * *